US012766155B2

(12) United States Patent
Wang

(10) Patent No.: US 12,766,155 B2
(45) Date of Patent: Oct. 20, 2026

(54) METHODS OF DECREASING HEPARAN SULFATE EXPRESSION USING EXT1 INHIBITORS

(71) Applicant: University of South Florida, Tampa, FL (US)

(72) Inventor: Lianchun Wang, Tampa, FL (US)

(73) Assignee: University of South Florida, Tampa, FL (US)

( * ) Notice: Subject to any disclaimer, the term of this patent is extended or adjusted under 35 U.S.C. 154(b) by 322 days.

(21) Appl. No.: 18/593,135

(22) Filed: Mar. 1, 2024

(65) Prior Publication Data

US 2024/0316067 A1 Sep. 26, 2024

Related U.S. Application Data

(60) Provisional application No. 63/599,754, filed on Nov. 16, 2023, provisional application No. 63/487,949, filed on Mar. 2, 2023.

(51) Int. Cl.
*A61K 31/593* (2006.01)
*A61K 45/06* (2006.01)

(52) U.S. Cl.
CPC ............ *A61K 31/593* (2013.01); *A61K 45/06* (2013.01)

(58) Field of Classification Search
CPC .... A61K 31/593; A61K 45/06; A61K 31/337; A61K 31/59; A61K 31/592
See application file for complete search history.

(56) References Cited

U.S. PATENT DOCUMENTS

2010/0048638 A1 2/2010 Crawford et al.
2010/0152140 A1 6/2010 Koo et al.

FOREIGN PATENT DOCUMENTS

WO 2021081448 A1 4/2021
WO 2024011161 A1 1/2024

OTHER PUBLICATIONS

Segovia-Mendoza et al (Int. J. Mol. Sci. 2021, 22, 12741, 1-36). (Year: 2021).*
Gu, Tingting, et al. "CREB is a novel nuclear target of PTEN phosphatase." Cancer research 71.8 (2011): 2821-2825.
Steven, André, et al. "What turns CREB on? and off? and why does it matter?." Cellular and Molecular Life Sciences 77 (2020): 4049-4067.
Ferguson, Brent W., and Sumana Datta. "Role of heparan sulfate 2-o-sulfotransferase in prostate cancer cell proliferation, invasion, and growth factor signaling." Prostate cancer 2011.1 (2011): 893208. pages 1-14.
Feng, Shu, et al. "Combination treatment of prostate cancer with FGF receptor and AKT kinase inhibitors." Oncotarget 8.4 (2016): 6179.
Daniel, Paul M., et al. "PI3K activation in neural stem cells drives tumorigenesis which can be ameliorated by targeting the cAMP response element binding protein." Neuro-oncology 20.10 (2018): 1344-1355.
Sapio, Luigi, et al. "Targeting CREB in cancer therapy: a key candidate or one of many? An update." Cancers 12.11 (2020): 3166.
Wan, Xiaofeng, et al. "AKT1-CREB stimulation of PDGFRα expression is pivotal for PTEN deficient tumor development." Cell Death & Disease 12.2 (2021): 172.
Nagarajan, Arvindhan, Parmanand Malvi, and Narendra Wajapeyee. "Heparan sulfate and heparan sulfate proteoglycans in cancer initiation and progression." Frontiers in endocrinology 9 (2018): 483.
Jamaspishvili, T., Berman, D., Ross, A. et al. Clinical implications of PTEN loss in prostate cancer. Nat Rev Urol 15, 222-234 (2018). https://doi.org/10.1038/nrurol.2018.9.
De Pasquale, Valeria, and Luigi Michele Pavone. "Heparan sulfate proteoglycan signaling in tumor microenvironment." International Journal of Molecular Sciences 21.18 (2020): 6588.
Watson, M. J., et al. "Aberrant CREB1 activation in prostate cancer disrupts normal prostate luminal cell differentiation." Oncogene 40.18 (2021): 3260-3272.
Aucoin, Rebecca, et al. "Dominant-negative CREB inhibits heparanase functionality and melanoma cell invasion." Journal of cellular biochemistry 93.2 (2004): 215-223.
Suhovskih, Anastasia V., et al. "Transcriptional activity of heparan sulfate biosynthetic machinery is specifically impaired in benign prostate hyperplasia and prostate cancer." Frontiers in Oncology 4 (2014): 79.
Tomlins SA, et al. Integrative molecular concept modeling of prostate cancer progression. Nat Genet. 2007;39(1):41-51.
Mantamadiotis T, et al. CREB signaling in neural stem/progenitor cells: Recent developments and the implications for brain tumor biology. Bioessays. 2012;34(4):293-300.
Fang, Lei-Ya, et al. "Infiltrating macrophages promote prostate tumorigenesis via modulating androgen receptor-mediated CCL4-STAT3 signaling." Cancer research 73.18 (2013): 5633-5646.
Giacomini, Arianna, et al. "The FGF/FGFR system in the physiopathology of the prostate gland." Physiological reviews 101.2 (2021): 569-610.
International Search Report and Written Opinion for International Application No. PCT/US2023/069689, dated Dec. 18, 2023, 17 Pages.

* cited by examiner

*Primary Examiner* — Kamal A Saeed
*Assistant Examiner* — Meghan C Heasley
(74) *Attorney, Agent, or Firm* — Meunier Carlin & Curfman LLC

(57) ABSTRACT

The present disclosure provides for a method of decreasing heparan sulfate expression in a subject in need thereof, the method comprising administering an inhibitor of EXT1 gene expression, wherein the inhibitor comprises a therapeutically effective amount of vitamin D. Further provided herein, is a method of treating cancer in a subject in need thereof, the method comprising administering an inhibitor of EXT1 gene expression, wherein the inhibitor comprises a therapeutically effective amount of vitamin D.

20 Claims, 12 Drawing Sheets

METHODS OF DECREASING HEPARAN SULFATE EXPRESSION USING EXT1 INHIBITORS

CROSS-REFERENCE TO RELATED APPLICATIONS

This application claims the benefit of priority to, and the benefit of, U.S. Provisional Application No. 63/599,754 filed on Nov. 16, 2023, and U.S. Provisional No. 63/487,949 filed on Mar. 2, 2023, the disclosures of which are hereby expressly incorporated by reference herein in its entirety.

STATEMENT OF GOVERNMENT SUPPORT

This invention was made with government support under Grant No. 5U01CA225784-05, awarded by the National Institute of Health and the National Cancer Institute. The government has certain rights in the invention.

BACKGROUND

Heparan sulfate is a linear polysaccharide. Previously, it was largely unknown how heparan sulfate expression was regulated and targeted to control biological functions. There is a need for drugs that can regulate heparan sulfate-related gene expression. The methods disclosed herein address these and other needs.

SUMMARY

In accordance with the purposes of the disclosed materials and methods, as embodied and broadly described herein, the disclosed subject matter, in one aspect, relates to heparan sulfate (HS) expression.

Thus, in one example, a method of decreasing heparan sulfate expression in a subject in need thereof is provided, including administering an inhibitor of EXT1 gene expression, wherein the inhibitor comprises a therapeutically effective amount of vitamin D.

In a further example, a method of treating cancer in a subject in need thereof is provided, including administering an inhibitor of EXT1 gene expression, wherein the inhibitor comprises a therapeutically effective amount of vitamin D.

Additional advantages will be set forth in part in the description that follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying figures, which are incorporated in and constitute a part of this specification, illustrate several aspects described below.

FIGS. 7A and 7B show the effect of vitamin D3 (D3) and calcitriol (Cal) on EXT1 mRNA expression in human M-17 cells. FIG. 7A shows effect of vitamin D3 on EXT1 and FIG. 7B shows the effect of calcitriol on EXT1. FIGS. 7C and 7D show the effect of artesunate (AS) and zinc pyritione (ZPT) on HS3ST1 mRNA expression in human M-17 cells. Note that *$p<0.05$, $p<0.01$, *$p<0.001$

FIG. 11A shows drug potential distribution or HS3ST1 cell line. FIG. 11B shows drug potential distribution for HS3ST2 cell line. FIG. 11C shows drug potential distribution for HS2ST1 cell line. FIG. 11D shows drug potential distribution for HS3ST4 cell line. FIG. 11E shows drug potential distribution for EXT1 cell line. FIG. 11F shows drug potential distribution for HS6ST1 cell line. Orange represents no potential drugs, maroon represents inhibition potential drugs, and purple represents activation potential drugs.

FIG. 12A shows inhibitory drugs specific for HS3ST1 cell line. FIG. 12B shows inhibitory drugs specific for HS3ST2 cell line. FIG. 12C shows inhibitory drugs specific for HS3ST4 cell line. FIG. 12D shows inhibitory drugs specific for HS6ST1 cell line. FIG. 12E shows inhibitory drugs specific for HS2ST1 cell line. FIG. 12F shows inhibitory drugs specific for EXT1 cell line. Maroon represents not specific, and blue is specific for cell line.

FIG. 13A shows the bortezomib-HS3ST1 reporter. FIG. 13B shows the CCK-8 results for HS3ST1 cell line using bortezomib. FIG. 13C shows the cytotoxicity results for HS3St1 cell line using bortezomib.

FIG. 14A shows the zinc pyrithione-HS3ST1 reporter. FIG. 14B shows the CCk-8 results for HS3ST1 cell line using zinc pyrithione. FIG. 14C shows the cytotoxicity results for HS3ST1 cell line using zinc pyrithione.

FIG. 15A shows the CCK-8 results for HS3ST1 cell line using artesunate. FIG. 15B shows the cytotoxicity results for HS3ST1 cell line using artesunate.

DETAILED DESCRIPTION

Figure 1:
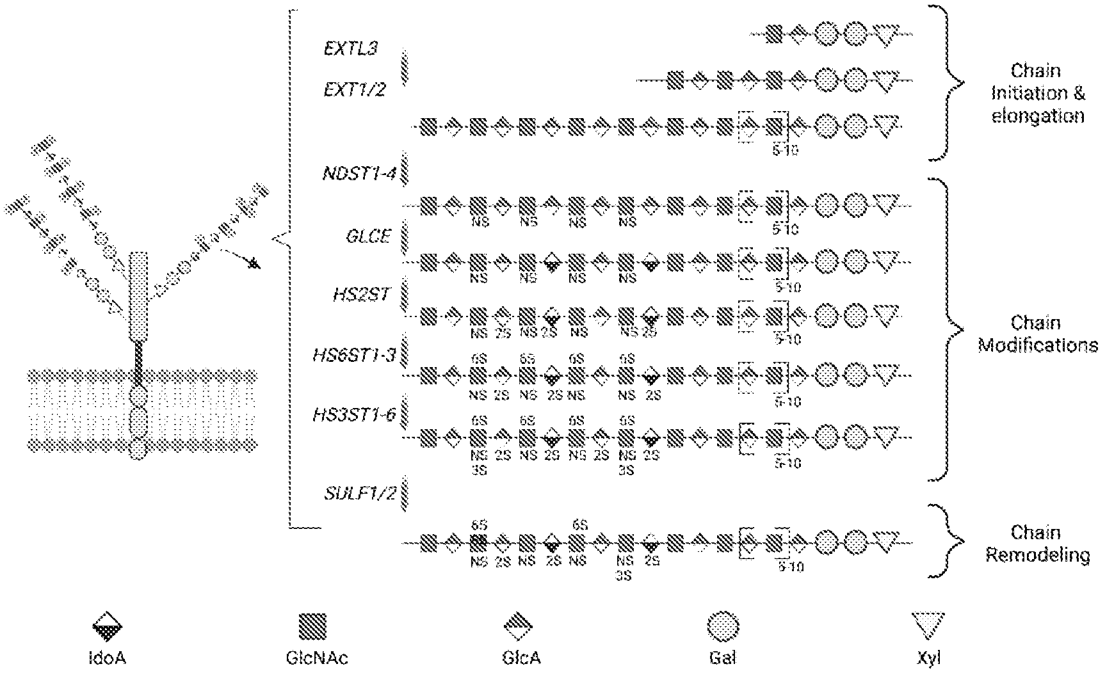
FIG. 1 shows HS chain initiation and elongation, chain modifications, and chain remodeling of select cell lines.

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a compound", "a composition", or "a disorder", includes, but is not limited to, two or more such compounds, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g., the phrase "x to y" includes the range from 'x' to 'y' as well as the range greater than 'x' and less than 'y'. The range can also be expressed as an upper limit, e.g., 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise. As used herein, the term "substantially free," when used in the context of a composition or component of a composition that is substantially absent, is intended to refer to an amount that is then about 1% by weight or less, e.g., less than about 0.5% by weight, less than about 0.1% by weight, less than about 0.05% by weight, or less than about 0.01% by weight of the stated material, based on the total weight of the composition.

The term "subject" preferably refers to a human in need of treatment with an anti-cancer agent or treatment for any purpose, and more preferably a human in need of such a treatment to treat cancer, or a precancerous condition or lesion. However, the term "patient" can also refer to non-human animals, preferably mammals such as dogs, cats, horses, cows, pigs, sheep and non-human primates, among others, that are in need of treatment with an anti-cancer agent or treatment.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control (e.g., an untreated tumor).

The term "treating" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "therapeutically effective" refers to the amount of the composition used is of sufficient quantity to ameliorate one or more causes or symptoms of a disease or disorder. Such amelioration only requires a reduction or alteration, not necessarily elimination.

Methods

Method of Decreasing Heparan Sulfate Expression-EXT1

The present disclosure, in one aspect, provides for a method of decreasing heparan sulfate expression in a subject in need thereof, the method comprising administering an inhibitor of EXT1 gene expression, wherein the inhibitor comprises a therapeutically effective amount of vitamin D.

Vitamin D refers to a group of fat-soluble secosteroids that includes naturally occurring and synthetic vitamin D compounds. Types of vitamin D include vitamin D1 (mixture of molecular compounds ergocalciferol and lumisterol), vitamin D2 (ergocalciferol, which can be made from ergosterol), vitamin D3 (cholecalciferol), vitamin D4 (22-dihydroergocalciferol), and vitamin D5 (sitocalciferol).

Furthermore, vitamin D includes vitamin D analogs, such as calcitriol, alfacalcidol, calcipotriol, doxercalciferol, falecalcitriol, paricalcitol, and tacalcitol.

In some examples, vitamin D is vitamin D3, calcitriol, or any combination thereof. In further examples, vitamin D is vitamin D3. In specific examples, vitamin D is calcitriol.

Vitamin D3, also known as cholecalciferol, is a type of vitamin D having the following chemical structure:

Formula I

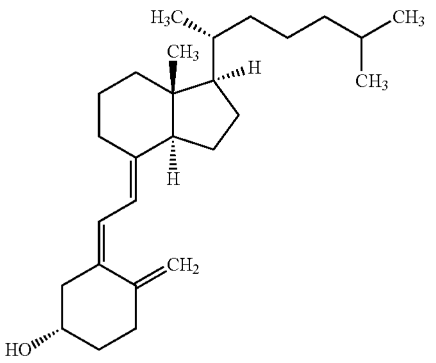

Calcitriol is a synthetic vitamin D analog, also known as 1, 25-dihydroxycholecalciferol. Calcitriol has the following chemical structure:

Formula II

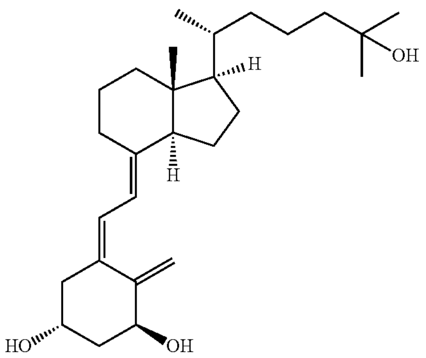

In certain examples, the therapeutically effective amount is from 0.2 microliters (μL) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 μL to 1 μL or 1 μL to 1.5 μL. In specific examples, the therapeutically effective amount is from 0.5 μL to 0.75 μL, 0.75 μL to 1 μL, 1 μL to 1.25 μL, or 1.25 μL to 1.5 μL. In certain examples, the therapeutically effective amount is from 0.5 μL to 1.25 μL.

In some examples, the therapeutically effective amount is from 0.8 μL to 0.9 μL, 0.9 μL to 1.0 μL, 1.0 μL to 1.1 μL, or 1.1 μL to 1.2 μL. In further examples, the therapeutically effective amount is from 0.8 μL to 0.85 μL, 0.85 to 0.9 μL, 0.9 μL to 0.95 μL, 0.95 μL to 1.0 μL, 1.0 μL to 1.05 μL, 1.05 μL to 1.10 μL, 1.10 μL to 1.15 μL, or 1.15 μL to 1.20 μL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

In specific examples, the vitamin D3 has an IC50 value of from 0.900 to 1.00. In certain examples, the IC50 value is from 0.950 to 0.975. In some examples, the IC50 value is from 0.960 to 0.965.

In some examples, the vitamin D3 has an IC50 value of from 0.900 to 0.910, 0.910 to 0.920, 0.920 to 0.930, 0.930 to 0.940, 0.940 to 0.950, 0.950 to 0.960, 0.960 to 0.970, 0.970 to 0.980, 0.980 to 0.990, or 0.990 to 1.000. In further examples, the vitamin D3 has an IC50 value of from 0.900 to 0.920, 0.900 to 0.930, 0.900 to 0.940, 0.900 to 0.950, 0.900 to 0.960, 0.900 to 0.970, 0.900 to 0.980, or 0.900 to 0.990.

In some examples, the IC50 value is from 0.950 to 0.955, 0.955 to 0.960, 0.960 to 0.965, 0.965 to 0.970, or 0.970 to 0.975. In further examples, the IC50 value is from 0.950 to 0.960, 0.950 to 0.965, or 0.950 to 0.970.

In certain examples, the IC50 value is from 0.960 to 0.961, 0.961 to 0.962, 0.962 to 0.963, 0.963 to 0.964, or 0.964 to 0.965. In specific examples, the IC50 value is from 0.960 to 0.962, 0.960 to 0.963, or 0.963 to 0.964.

In further examples, the calcitriol has an IC50 value of from 0.900 to 1.00. In specific examples, the IC50 value is from 0.950 to 0.975. In certain examples, the IC50 value is from 0.965 to 0.970.

In some examples, the calcitriol has an IC50 value of from 0.900 to 0.910, 0.910 to 0.920, 0.920 to 0.930, 0.930 to 0.940, 0.940 to 0.950, 0.950 to 0.960, 0.960 to 0.970, 0.970 to 0.980, 0.980 to 0.990, or 0.990 to 1.000. In further examples, the calcitriol has an IC50 value of from 0.900 to 0.920, 0.900 to 0.930, 0.900 to 0.940, 0.900 to 0.950, 0.900 to 0.960, 0.900 to 0.970, 0.900 to 0.980, or 0.900 to 0.990.

In some examples, the IC50 value is from 0.950 to 0.955, 0.955 to 0.960, 0.960 to 0.965, 0.965 to 0.970, or 0.970 to 0.975. In further examples, the IC50 value is from 0.950 to 0.960, 0.950 to 0.965, or 0.950 to 0.970.

In certain examples, the IC50 value is from 0.960 to 0.961, 0.961 to 0.962, 0.962 to 0.963, 0.963 to 0.964, or 0.964 to 0.965. In specific examples, the IC50 value is from 0.960 to 0.962, 0.960 to 0.963, or 0.963 to 0.964.

Method of Treating Cancer EXT1

Further provided herein is a method of treating cancer in a subject in need thereof, the method comprising administering an inhibitor of EXT1 gene expression, wherein the inhibitor comprises a therapeutically effective amount of vitamin D.

In some examples, vitamin D is vitamin D3, calcitriol, or any combination thereof. In further examples, vitamin D is vitamin D3. In specific examples, vitamin D is calcitriol.

In certain examples, the therapeutically effective amount is from 0.2 microliters (μL) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 μL to 1 μL or 1 μL to 1.5 μL. In specific examples, the therapeutically effective amount is from 0.5 μL to 0.75 μL, 0.75 μL to 1 μL, 1 μL to 1.25 μL, or 1.25 μL to 1.5 μL. In certain examples, the therapeutically effective amount is from 0.5 μL to 1.25 μL.

In some examples, the therapeutically effective amount is from 0.8 μL to 0.9 μL, 0.9 μL to 1.0 μL, 1.0 μL to 1.1 μL, or 1.1 μL to 1.2 μL. In further examples, the therapeutically effective amount is from 0.8 μL to 0.85 μL, 0.85 to 0.9 μL, 0.9 μL to 0.95 μL, 0.95 μL to 1.0 μL, 1.0 μL to 1.05 μL, 1.05 μL to 1.10 μL, 1.10 μL to 1.15 μL, or 1.15 μL to 1.20 μL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

In specific examples, the inhibitor is administered in combination with a cancer therapy. In certain examples, the cancer therapy comprises surgery, chemotherapy, immunotherapy, ionizing radiation, or a combination thereof.

In some examples, surgery includes curative surgery, preventive surgery, diagnostic surgery, staging surgery, debulking surgery, palliative surgery, supportive surgery, and restorative surgery, as well as cryosurgery, laser surgery, electrosurgery, and microscopically controlled surgery.

In some examples, chemotherapy can include R-CHOP (Rituxan, cyclophosphamide, doxorubicin, vincristine, and prednisone), VcR-CAP (bortezomib, rituximab, cyclophosphamide, doxorubicin, and prednisone), R-hyperCVAD (rituximab, cyclophosphamide, vincristine, doxorubicin, and dexamethasone alternating with high-dose cytarabine and methotrexate), B+R (bendamustine and rituximab), R-FCM (rituximab, fludarabine, cyclophosphamide, and mitoxantrone), R-DHAP (rituximab, dexamethasone, cytarabine and cisplatin), R-CVP (rituximab, cyclophosphamide, vincristine, and prednisone), or R-CBP (rituximab, cyclophosphamide, bortezomib, and prednisone), or any combination thereof. These chemotherapies can be administered intravenously or via mouth.

In some examples, immunotherapy includes monoclonal antibodies, checkpoint inhibitors, CAR T-cell therapy, and cytokines.

In further examples, ionizing radiation includes radiation therapy using high-energy particles or waves, x-rays, gamma rays, electron beams, or protons.

In some examples, the surgery comprises stem cell transplantation (SCT). In specific examples, the surgery comprises stem cell transplantation (SCT). Stem cell transplantation (SCT), also referred to as a bone marrow transplant, is a procedure in which a subject receives healthy stem cells to replace damaged stem cells. This can include autologous transplantation in which the transplantation uses the subject's own stem cells. SCT can also include allogeneic transplantation, which uses stem cells from a donor.

In autologous transplantation, the subject stem cells are collected and stored. The cells are frozen and then returned to the subject after receiving intensive high-dose chemotherapy cither with or without radiation therapy. This procedure can be used in clinically symptomatic subjects that are fit, young, and have few or no coexisting illnesses.

In further examples, cancer therapy can include R-CHOP followed by an autologous SCT, R-CHOP followed by higher doses of cytarabine and further followed by an autologous stem cell transplant, or R-hyperCVAD with autologous SCT, or any combination thereof.

In further examples, the method further comprises administering an additional therapeutic agent. In specific examples, the additional therapeutic agent comprises abiraterone acetate, apalutamide, bicalutamide, cabazitaxel, darolutamide, degarelix, docetaxel, enzalutamide, flutamide, goserelin acetate, leuprolide acetate, lutetium Lu 177 vipivotide tetraxetan, mitoxantrone hydrochloride, nilutamide, olaparib, radium 223 dichloride, relugolix, rucaparib camsylate, sipuleucel-t, or any combination thereof.

In certain examples, the cancer is a solid tumor. Solid tumors that are cancerous are mainly of monoclonal origin and manifest six essential alterations: growth signals, intensification of anti-growth signals, cell and tissue apoptosis or necrosis, limitless replicative and proliferative potential, prolonged angiogenesis, and organ/tissue invasion followed by metastasis. Solid tumors can include adenocarcinoma, small cell carcinoma, neuroendocrine tumor, transitional cell carcinoma, or sarcoma, as described below.

In some examples, the cancer comprises Stage I, Stage II, Stage III, or Stage IV cancer.

Stage I means the cancer is small and only in one area. This is also called early-stage cancer. Stage II and III mean the cancer is larger and has grown into nearby tissues or lymph nodes. Stage IV means the cancer has spread to other parts of the body and can also be called advanced or metastatic cancer.

In further examples, the cancer comprises adenocarcinoma, small cell carcinoma, neuroendocrine tumor, transitional cell carcinoma, sarcoma, or any combination thereof.

Adenocarcinomas develop in gland cells that line the area impacted by the cancer.

Small cell carcinomas develop from neuroendocrine cells.

A neuroendocrine tumor is an aggressive histologic subtype of cancer and most commonly arises in later stages of cancer as a mechanism of treatment resistance.

Sarcomas are a heterogenous group of tumors arising from mesenchymal cells in and around the area impacted by the cancer.

Method of Decreasing Heparan Sulfate Expression-HS3ST1

The present disclosure, in one aspect, provides for a method of decreasing heparan sulfate expression in a subject in need thereof, the method comprising administering an inhibitor of HS3ST1 gene expression, wherein the inhibitor comprises a therapeutically effective amount of bortezomib.

Bortezomib refers to an antineoplastic agent that interferes with the growth of cancer cells. In some examples, it can be administered intravenously or subcutaneously. Bortezomib has the following chemical structure:

Formula III

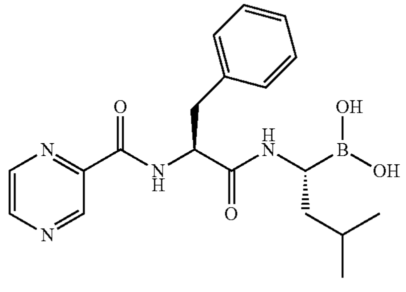

In certain examples, the therapeutically effective amount is from 0.2 microliters (μL) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 μL to 1 μL or 1 μL to 1.5 μL. In specific examples, the therapeutically effective amount is from 0.5 μL to 0.75 μL, 0.75 μL to 1 μL, 1 μL to 1.25 μL, or 1.25 μL to 1.5 μL. In certain examples, the therapeutically effective amount is from 0.5 μL to 1.25 μL.

In some examples, the therapeutically effective amount is from 0.8 μL to 0.9 μL, 0.9 μL to 1.0 μL, 1.0 μL to 1.1 μL, or 1.1 μL to 1.2 μL. In further examples, the therapeutically effective amount is from 0.8 μL to 0.85 μL, 0.85 to 0.9 μL, 0.9 μL to 0.95 μL, 0.95 μL to 1.0 μL, 1.0 μL to 1.05 μL, 1.05 μL to 1.10 μL, 1.10 μL to 1.15 μL, or 1.15 μL to 1.20 μL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

In specific examples, the bortezomib has an IC50 value of from 0.900 to 1.00. In certain examples, the IC50 value is from 0.900 to 0.950. In some examples, the IC50 value is from 0.910 to 0.925.

In some examples, the bortezomib has an IC50 value of from 0.900 to 0.910, 0.910 to 0.920, 0.920 to 0.930, 0.930 to 0.940, 0.940 to 0.950, 0.950 to 0.960, 0.960 to 0.970, 0.970 to 0.980, 0.980 to 0.990, or 0.990 to 1.000. In further examples, the bortezomib has an IC50 value of from 0.900 to 0.920, 0.900 to 0.930, 0.900 to 0.940, 0.900 to 0.950, 0.900 to 0.960, 0.900 to 0.970, 0.900 to 0.980, or 0.900 to 0.990.

In some examples, the bortezomib has an IC50 value is from 0.900 to 0.905, 0.905 to 0.910, 0.910 to 0.915, 0.915 to 0.920, or 0.920 to 0.925. In further examples, the IC50 value is from 0.910 to 0.915, 0.910 to 0.920, or 0.910 to 0.925.

In certain examples, the bortezomib has an IC50 value is from 0.915 to 0.916, 0.916 to 0.917, 0.917 to 0.918, 0.918 to 0.919, or 0.919 to 0.920. In specific examples, the IC50 value is from 0.915 to 0.917, 0.915 to 0.918, or 0.915 to 0.919.

The present disclosure, in one aspect, provides for a method of decreasing heparan sulfate expression in a subject in need thereof, the method comprising administering an inhibitor of HS3ST1 gene expression, wherein the inhibitor comprises a therapeutically effective amount of zinc pyrithione.

Zinc pyrithione refers to a coordination complex of zinc that has fungistatic and bacteriostatic properties. Zinc pyrithione has the following chemical structure:

Formula IV

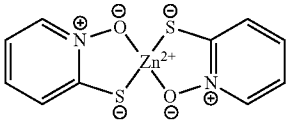

In certain examples, the therapeutically effective amount is from 0.2 microliters (μL) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 µL to 1 µL or 1 µL to 1.5 µL. In specific examples, the therapeutically effective amount is from 0.5 µL to 0.75 µL, 0.75 µL to 1 µL, 1 µL to 1.25 µL, or 1.25 µL to 1.5 µL. In certain examples, the therapeutically effective amount is from 0.5 µL to 1.25 µL.

In some examples, the therapeutically effective amount is from 0.8 µL to 0.9 µL, 0.9 µL to 1.0 µL, 1.0 µL to 1.1 µL, or 1.1 µL to 1.2 µL. In further examples, the therapeutically effective amount is from 0.8 µL to 0.85 µL, 0.85 to 0.9 µL, 0.9 µL to 0.95 µL, 0.95 µL to 1.0 µL, 1.0 µL to 1.05 µL, 1.05 µL to 1.10 µL, 1.10 µL to 1.15 µL, or 1.15 µL to 1.20 µL. In certain examples, the therapeutically effective amount is from 0.8 µL to 1.0 µL or 0.8 µL to 1.1 µL. In specific examples, the therapeutically effective amount is from 0.8 µL to 0.9 µL, 0.8 µL to 0.95 µL, 0.8 µL to 1.05 µL, 0.8 µL to 1.10 µL, or 0.8 µL to 1.15 µL.

In specific examples, the zinc pyrithione has an IC50 value of from $1.300\times10^{-7}$ to $1.400\times10^{-7}$. In certain examples, the IC50 value is from $1.350\times10^{-7}$ to $1.400\times10^{-7}$. In some examples, the IC50 value is from $1.360\times10^{-7}$ to $1.380\times10^{-7}$.

In some examples, the zinc pyrithione has an IC50 value is from $1.360\times10^{-7}$ to $1.365\times10^{-7}$, $1.365\times10^{-7}$ to $1.370\times10^{-7}$, $1.370\times10^{-7}$ to $1.375\times10^{-7}$, or $1.375\times10^{-7}$ to $1.380\times10^{-7}$.

The present disclosure, in one aspect, provides for a method of decreasing heparan sulfate expression in a subject in need thereof, the method comprising administering an inhibitor of HS3ST1 gene expression, wherein the inhibitor comprises a therapeutically effective amount of artesunate.

Artesunate refers to an antimalarial drug. In some examples, artesunate is administered by injecting into a vein, injection into a muscle, by mouth, or by rectum. Artesunate has the following chemical structure:

Formula V

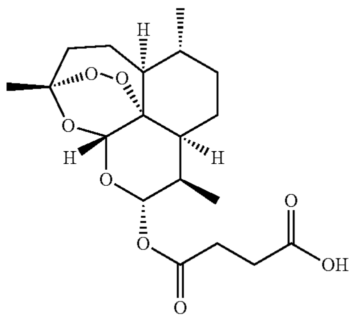

In certain examples, the therapeutically effective amount is from 0.2 microliters (µL) to 10 µL. In some examples, the therapeutically effective amount is from 0.5 µL to 1.5 µL. In further examples, the therapeutically effective amount is from 0.8 µL to 1.2 µL.

In further examples, the therapeutically effective amount is from 0.5 µL to 1 µL or 1 µL to 1.5 µL. In specific examples, the therapeutically effective amount is from 0.5 µL to 0.75 µL, 0.75 µL to 1 µL, 1 µL to 1.25 µL, or 1.25 µL to 1.5 µL. In certain examples, the therapeutically effective amount is from 0.5 µL to 1.25 µL.

In some examples, the therapeutically effective amount is from 0.8 µL to 0.9 µL, 0.9 µL to 1.0 µL, 1.0 µL to 1.1 µL, or 1.1 µL to 1.2 µL. In further examples, the therapeutically effective amount is from 0.8 µL to 0.85 µL, 0.85 to 0.9 µL, 0.9 µL to 0.95 µL, 0.95 µL to 1.0 µL, 1.0 µL to 1.05 µL, 1.05 µL to 1.10 µL, 1.10 µL to 1.15 µL, or 1.15 µL to 1.20 µL. In certain examples, the therapeutically effective amount is from 0.8 µL to 1.0 µL or 0.8 µL to 1.1 µL. In specific examples, the therapeutically effective amount is from 0.8 µL to 0.9 µL, 0.8 µL to 0.95 µL, 0.8 µL to 1.05 µL, 0.8 µL to 1.10 µL, or 0.8 µL to 1.15 µL.

In specific examples, the artesunate has an IC50 value of from $4.5\times10^{-35}$ to $5.0\times10^{-35}$. In certain examples, the IC50 value is from $4.65\times10^{-35}$ to $4.85\times10^{-35}$. In some examples, the IC50 value is from $4.7\times10^{-35}$ to $4.8\times10^{-35}$.

In some examples, the artesunate has an IC50 value is from $4.5\times10^{-35}$ to $4.6\times10^{-35}$, $4.6\times10^{-35}$ to $4.7\times10^{-35}$, $4.7\times10^{-35}$ to $4.8\times10^{-35}$, $4.8\times10^{-35}$ to $4.9\times10^{-35}$, or $4.9\times10^{-35}$ to $5.0\times10^{-35}$. In some examples, the artesunate has an IC50 value is from $4.5\times10^{-35}$ to $4.7\times10^{-35}$, $4.5\times10^{-35}$ to $4.8\times10^{-35}$, or $4.5\times10^{-35}$ to $4.9\times10^{-35}$. In certain examples, the IC50 value is from $4.65\times10^{-35}$ to $4.75\times10^{-35}$ or $4.75\times10^{-35}$ to $4.85\times10^{-35}$. In some examples, the IC50 value is from $4.7\times10^{-35}$ to $4.72\times10^{-35}$, $4.72\times10^{-35}$ to $4.74\times10^{-35}$, $4.74\times10^{-35}$ to $4.76\times10^{-35}$, $4.76\times10^{-35}$ to $4.78\times10^{-35}$, or $4.78\times10^{-35}$ to $4.8\times10^{-35}$. In further examples, $4.70\times10^{-35}$ to $4.74\times10^{-35}$, $4.70\times10^{-35}$ to $4.70\times10^{-35}$, or $4.70\times10^{-35}$ to $4.78\times10^{-35}$.

Method of Decreasing Heparan Sulfate Expression—HS3ST4

The present disclosure, in one aspect, provides for a method of decreasing heparan sulfate expression in a subject in need thereof, the method comprising administering an inhibitor of HS3ST4 gene expression, wherein the inhibitor comprises a therapeutically effective amount of fosbretabulin.

Fosbretabulin refers to a microtubule, which is a type of vascular-targeting agent. In some examples, fosbretabulin has antineoplastic activity. Fosbretabulin has the following chemical structure:

Formula VI

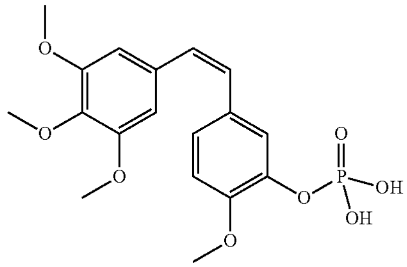

In certain examples, the therapeutically effective amount is from 0.2 microliters (µL) to 10 µL. In some examples, the therapeutically effective amount is from 0.5 µL to 1.5 µL. In further examples, the therapeutically effective amount is from 0.8 µL to 1.2 µL.

In further examples, the therapeutically effective amount is from 0.5 µL to 1 µL or 1 µL to 1.5 µL. In specific examples, the therapeutically effective amount is from 0.5 µL to 0.75 µL, 0.75 µL to 1 µL, 1 µL to 1.25 µL, or 1.25 µL to 1.5 µL. In certain examples, the therapeutically effective amount is from 0.5 µL to 1.25 µL.

In some examples, the therapeutically effective amount is from 0.8 µL to 0.9 µL, 0.9 µL to 1.0 µL, 1.0 µL to 1.1 µL, or 1.1 µL to 1.2 µL. In further examples, the therapeutically effective amount is from 0.8 µL to 0.85 µL, 0.85 to 0.9 µL, 0.9 µL to 0.95 µL, 0.95 µL to 1.0 µL, 1.0 µL to 1.05 µL, 1.05 µL to 1.10 µL, 1.10 µL to 1.15 µL, or 1.15 µL to 1.20 µL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

The present disclosure, in one aspect, provides for a method of decreasing heparan sulfate expression in a subject in need thereof, the method comprising administering an inhibitor of HS3ST4 gene expression, wherein the inhibitor comprises a therapeutically effective amount of niclosamide.

Niclosamide refers to an oral anthelminthic drug used to treat parasitic infections. In some examples, niclosamide is taken by mouth. Niclosamide has the following chemical structure:

Formula VII

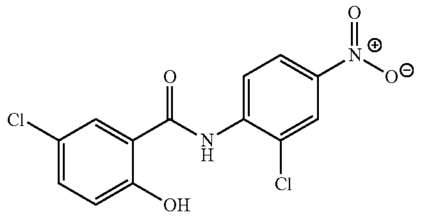

In certain examples, the therapeutically effective amount is from 0.2 microliters (L) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 μL to 1 μL or 1 μL to 1.5 μL. In specific examples, the therapeutically effective amount is from 0.5 μL to 0.75 μL, 0.75 μL to 1 μL, 1 μL to 1.25 μL, or 1.25 μL to 1.5 μL. In certain examples, the therapeutically effective amount is from 0.5 μL to 1.25 μL.

In some examples, the therapeutically effective amount is from 0.8 μL to 0.9 μL, 0.9 μL to 1.0 μL, 1.0 μL to 1.1 μL, or 1.1 μL to 1.2 μL. In further examples, the therapeutically effective amount is from 0.8 μL to 0.85 μL, 0.85 to 0.9 μL, 0.9 μL to 0.95 μL, 0.95 μL to 1.0 μL, 1.0 μL to 1.05 μL, 1.05 μL to 1.10 μL, 1.10 μL to 1.15 μL, or 1.15 μL to 1.20 μL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

Method of Treating Cancer-HS3ST1

Further provided herein is a method of treating cancer in a subject in need thereof, the method comprising administering an inhibitor of HS3ST1 gene expression, wherein the inhibitor comprises a therapeutically effective amount of bortezomib, zinc pyrithione, artesunate, or any combination thereof.

In certain examples, the therapeutically effective amount is from 0.2 microliters (μL) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 μL to 1 μL or 1 μL to 1.5 μL. In specific examples, the therapeutically effective amount is from 0.5 μL to 0.75 μL, 0.75 μL to 1 μL, 1 μL to 1.25 μL, or 1.25 μL to 1.5 μL. In certain examples, the therapeutically effective amount is from 0.5 μL to 1.25 μL.

In some examples, the therapeutically effective amount is from 0.8 μL to 0.9 μL, 0.9 μL to 1.0 μL, 1.0 μL to 1.1 μL, or 1.1 μL to 1.2 μL. In further examples, the therapeutically effective amount is from 0.8 μL to 0.85 μL, 0.85 to 0.9 μL, 0.9 μL to 0.95 μL, 0.95 μL to 1.0 μL, 1.0 μL to 1.05 μL, 1.05 μL to 1.10 μL, 1.10 μL to 1.15 μL, or 1.15 μL to 1.20 μL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

In specific examples, the inhibitor is administered in combination with a cancer therapy. In certain examples, the cancer therapy comprises surgery, chemotherapy, immunotherapy, ionizing radiation, or a combination thereof.

In some examples, surgery includes curative surgery, preventive surgery, diagnostic surgery, staging surgery, debulking surgery, palliative surgery, supportive surgery, and restorative surgery, as well as cryosurgery, laser surgery, electrosurgery, and microscopically controlled surgery.

In some examples, chemotherapy can include R-CHOP (Rituxan, cyclophosphamide, doxorubicin, vincristine, and prednisone), VcR-CAP (bortezomib, rituximab, cyclophosphamide, doxorubicin, and prednisone), R-hyperCVAD (rituximab, cyclophosphamide, vincristine, doxorubicin, and dexamethasone alternating with high-dose cytarabine and methotrexate), B+R (bendamustine and rituximab), R-FCM (rituximab, fludarabine, cyclophosphamide, and mitoxantrone), R-DHAP (rituximab, dexamethasone, cytarabine and cisplatin), R-CVP (rituximab, cyclophosphamide, vincristine, and prednisone), or R-CBP (rituximab, cyclophosphamide, bortezomib, and prednisone), or any combination thereof. These chemotherapies can be administered intravenously or via mouth.

In some examples, immunotherapy includes monoclonal antibodies, checkpoint inhibitors, CAR T-cell therapy, and cytokines.

In further examples, ionizing radiation includes radiation therapy using high-energy particles or waves, x-rays, gamma rays, electron beams, or protons.

In some examples, the surgery comprises stem cell transplantation (SCT). In specific examples, the surgery comprises stem cell transplantation (SCT). Stem cell transplantation (SCT), also referred to as a bone marrow transplant, is a procedure in which a subject receives healthy stem cells to replace damaged stem cells. This can include autologous transplantation in which the transplantation uses the subject's own stem cells. SCT can also include allogeneic transplantation, which uses stem cells from a donor.

In autologous transplantation, the subject stem cells are collected and stored. The cells are frozen and then returned to the subject after receiving intensive high-dose chemotherapy either with or without radiation therapy. This procedure can be used in clinically symptomatic subjects that are fit, young, and have few or no coexisting illnesses.

In further examples, cancer therapy can include R-CHOP followed by an autologous SCT, R-CHOP followed by higher doses of cytarabine and further followed by an autologous stem cell transplant, or R-hyperCVAD with autologous SCT, or any combination thereof.

In further examples, the method further comprises administering an additional therapeutic agent. In specific examples, the additional therapeutic agent comprises abiraterone acetate, apalutamide, bicalutamide, cabazitaxel, darolutamide, degarelix, docetaxel, enzalutamide, flutamide, goserelin acetate, leuprolide acetate, lutetium Lu 177 vipivotide tetraxetan, mitoxantrone hydrochloride, nilutamide, olaparib, radium 223 dichloride, relugolix, rucaparib camsylate, sipuleucel-t, or any combination thereof.

In certain examples, the cancer is a solid tumor. Solid tumors that are cancerous are mainly of monoclonal origin and manifest six essential alterations: growth signals, intensification of anti-growth signals, cell and tissue apoptosis or necrosis, limitless replicative and proliferative potential, prolonged angiogenesis, and organ/tissue invasion followed by metastasis. Solid tumors can include adenocarcinoma, small cell carcinoma, neuroendocrine tumor, transitional cell carcinoma, or sarcoma, as described below.

In some examples, the cancer comprises Stage I, Stage II, Stage III, or Stage IV cancer.

Stage I means the cancer is small and only in one area. This is also called early-stage cancer. Stage II and III mean the cancer is larger and has grown into nearby tissues or lymph nodes. Stage IV means the cancer has spread to other parts of the body and can also be called advanced or metastatic cancer.

In further examples, the cancer comprises adenocarcinoma, small cell carcinoma, neuroendocrine tumor, transitional cell carcinoma, sarcoma, or any combination thereof.

Adenocarcinomas develop in gland cells that line the area impacted by the cancer.

Small cell carcinomas develop from neuroendocrine cells.

A neuroendocrine tumor is an aggressive histologic subtype of cancer and most commonly arises in later stages of cancer as a mechanism of treatment resistance.

Sarcomas are a heterogenous group of tumors arising from mesenchymal cells in and around the area impacted by the cancer.

Method of Treating Cancer—HS3ST4

Further provided herein is a method of treating cancer in a subject in need thereof, the method comprising administering an inhibitor of HS3ST4 gene expression, wherein the inhibitor comprises a therapeutically effective amount of fosbretabulin, niclosamide, or any combination thereof.

In certain examples, the therapeutically effective amount is from 0.2 microliters (L) to 10 μL. In some examples, the therapeutically effective amount is from 0.5 μL to 1.5 μL. In further examples, the therapeutically effective amount is from 0.8 μL to 1.2 μL.

In further examples, the therapeutically effective amount is from 0.5 μL to 1 μL or 1 μL to 1.5 μL. In specific examples, the therapeutically effective amount is from 0.5 μL to 0.75 μL, 0.75 μL to 1 μL, 1 μL to 1.25 μL, or 1.25 μL to 1.5 μL. In certain examples, the therapeutically effective amount is from 0.5 μL to 1.25 μL.

In some examples, the therapeutically effective amount is from 0.8 μL to 0.9 μL, 0.9 μL to 1.0 μL, 1.0 μL to 1.1 μL, or 1.1 μL to 1.2 μL. In further examples, the therapeutically effective amount is from 0.8 μL to 0.85 μL, 0.85 to 0.9 μL, 0.9 μL to 0.95 μL, 0.95 μL to 1.0 μL, 1.0 μL to 1.05 μL, 1.05 μL to 1.10 μL, 1.10 μL to 1.15 μL, or 1.15 μL to 1.20 μL. In certain examples, the therapeutically effective amount is from 0.8 μL to 1.0 μL or 0.8 μL to 1.1 μL. In specific examples, the therapeutically effective amount is from 0.8 μL to 0.9 μL, 0.8 μL to 0.95 μL, 0.8 μL to 1.05 μL, 0.8 μL to 1.10 μL, or 0.8 μL to 1.15 μL.

In specific examples, the inhibitor is administered in combination with a cancer therapy. In certain examples, the cancer therapy comprises surgery, chemotherapy, immunotherapy, ionizing radiation, or a combination thereof.

In some examples, surgery includes curative surgery, preventive surgery, diagnostic surgery, staging surgery, debulking surgery, palliative surgery, supportive surgery, and restorative surgery, as well as cryosurgery, laser surgery, electrosurgery, and microscopically controlled surgery.

In some examples, chemotherapy can include R-CHOP (Rituxan, cyclophosphamide, doxorubicin, vincristine, and prednisone), VcR-CAP (bortezomib, rituximab, cyclophosphamide, doxorubicin, and prednisone), R-hyperCVAD (rituximab, cyclophosphamide, vincristine, doxorubicin, and dexamethasone alternating with high-dose cytarabine and methotrexate), B+R (bendamustine and rituximab), R-FCM (rituximab, fludarabine, cyclophosphamide, and mitoxantrone), R-DHAP (rituximab, dexamethasone, cytarabine and cisplatin), R-CVP (rituximab, cyclophosphamide, vincristine, and prednisone), or R-CBP (rituximab, cyclophosphamide, bortezomib, and prednisone), or any combination thereof. These chemotherapies can be administered intravenously or via mouth.

In some examples, immunotherapy includes monoclonal antibodies, checkpoint inhibitors, CAR T-cell therapy, and cytokines.

In further examples, ionizing radiation includes radiation therapy using high-energy particles or waves, x-rays, gamma rays, electron beams, or protons.

In some examples, the surgery comprises stem cell transplantation (SCT). In specific examples, the surgery comprises stem cell transplantation (SCT). Stem cell transplantation (SCT), also referred to as a bone marrow transplant, is a procedure in which a subject receives healthy stem cells to replace damaged stem cells. This can include autologous transplantation in which the transplantation uses the subject's own stem cells. SCT can also include allogeneic transplantation, which uses stem cells from a donor.

In autologous transplantation, the subject stem cells are collected and stored. The cells are frozen and then returned to the subject after receiving intensive high-dose chemotherapy either with or without radiation therapy. This procedure can be used in clinically symptomatic subjects that are fit, young, and have few or no coexisting illnesses.

In further examples, cancer therapy can include R-CHOP followed by an autologous SCT, R-CHOP followed by higher doses of cytarabine and further followed by an autologous stem cell transplant, or R-hyperCVAD with autologous SCT, or any combination thereof.

In further examples, the method further comprises administering an additional therapeutic agent. In specific examples, the additional therapeutic agent comprises abiraterone acetate, apalutamide, bicalutamide, cabazitaxel, darolutamide, degarelix, docetaxel, enzalutamide, flutamide, goserelin acetate, leuprolide acetate, lutetium Lu 177 vipivotide tetraxetan, mitoxantrone hydrochloride, nilutamide, olaparib, radium 223 dichloride, relugolix, rucaparib camsylate, sipuleucel-t, or any combination thereof.

In certain examples, the cancer is a solid tumor. Solid tumors that are cancerous are mainly of monoclonal origin and manifest six essential alterations: growth signals, intensification of anti-growth signals, cell and tissue apoptosis or necrosis, limitless replicative and proliferative potential, prolonged angiogenesis, and organ/tissue invasion followed by metastasis. Solid tumors can include adenocarcinoma, small cell carcinoma, neuroendocrine tumor, transitional cell carcinoma, or sarcoma, as described below.

In some examples, the cancer comprises Stage I, Stage II, Stage III, or Stage IV cancer.

Stage I means the cancer is small and only in one area. This is also called early-stage cancer. Stage II and III mean the cancer is larger and has grown into nearby tissues or lymph nodes. Stage IV means the cancer has spread to other parts of the body and can also be called advanced or metastatic cancer.

In further examples, the cancer comprises adenocarcinoma, small cell carcinoma, neuroendocrine tumor, transitional cell carcinoma, sarcoma, or any combination thereof.

Adenocarcinomas develop in gland cells that line the area impacted by the cancer.

Small cell carcinomas develop from neuroendocrine cells.

A neuroendocrine tumor is an aggressive histologic subtype of cancer and most commonly arises in later stages of cancer as a mechanism of treatment resistance.

Sarcomas are a heterogenous group of tumors arising from mesenchymal cells in and around the area impacted by the cancer.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLE

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention, which are apparent to one skilled in the art.

Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1: Using a Novel High Throughput Screening Assay to Identify FDA-Approved Drugs that Regulate Heparan Sulfate Expression Heparan Sulfate (HS) is a linear polysaccharide with a variety of biological functions, including developmental processes, angiogenesis, blood coagulation, and tumor metastasis. Aberrant expression of the HS-biosynthesis and modification genes has been linked to many human diseases. Previously, it was largely unknown how HS expression was regulated and could be targeted. This example identified FDA-approved drugs which regulated HS-related gene expression using an innovative High Throughput Screening (HTS) assay.

Figure 2:
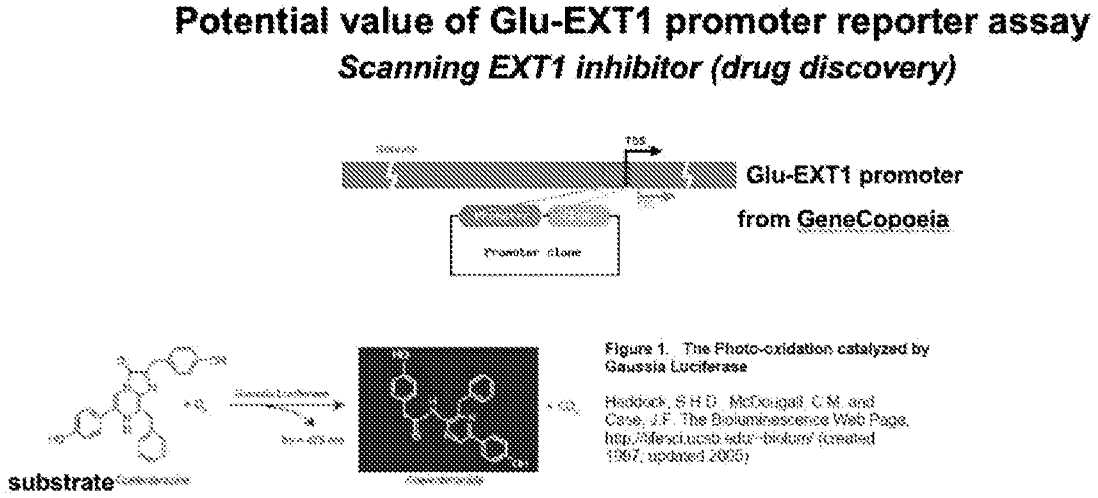
FIG. 2 shows the potential value of Glu-EXT1 promoter reporter assay for scanning EXT1 inhibitor.

Using a stable cell line with promoter luciferase reporter of the HS-biosynthetic gene EXT1, the EXT1 and other HS-biosynthetic gene reporter cell lines were screened with an FDA-approved drug library. (FIG. 1; FIG. 2)

Using EC-50 and CCK-8, Vitamin D3 and calcitriol (10 μL) were confirmed candidates when screened with respect to EXT1.

Figure 6:
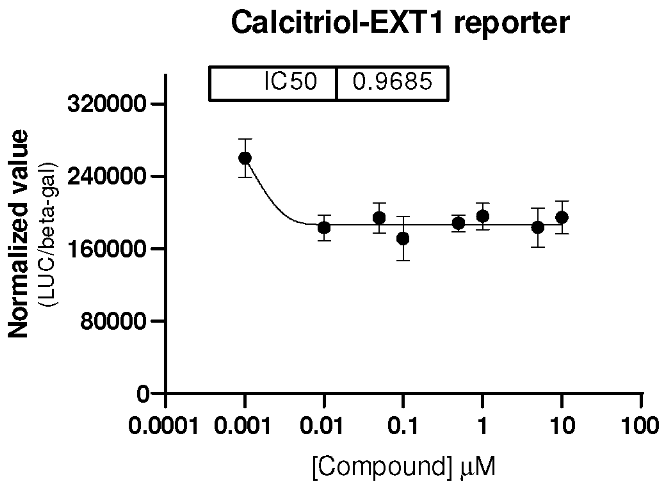
FIG. 6 shows an example calcitriol-EXT1 reporter.
Figure 7A:
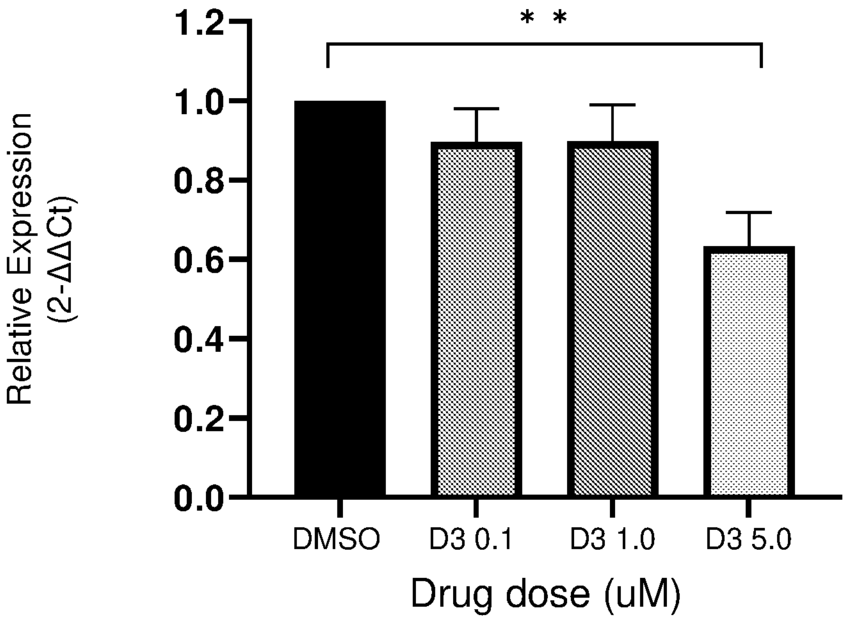
FIGS. 7A, 7B, 7C, and 7D shows the effect of screened drugs on mRna expression human M-17 cells.
Figure 7B:
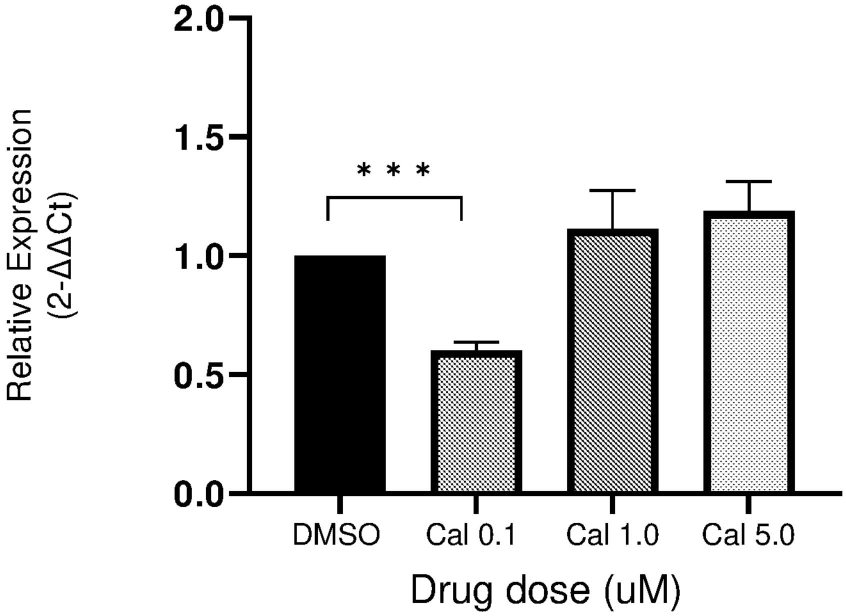
Figure 7C:
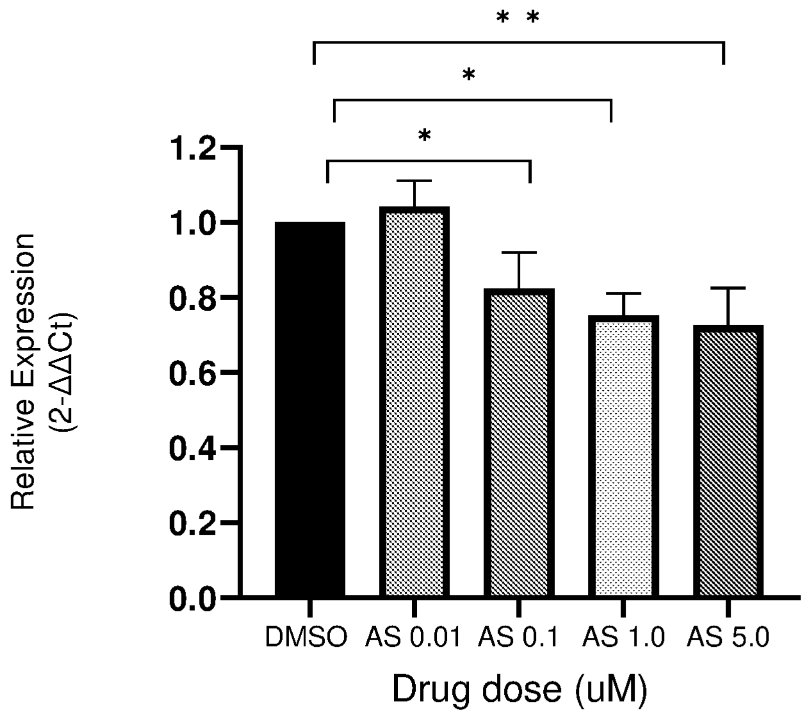
Figure 7D:
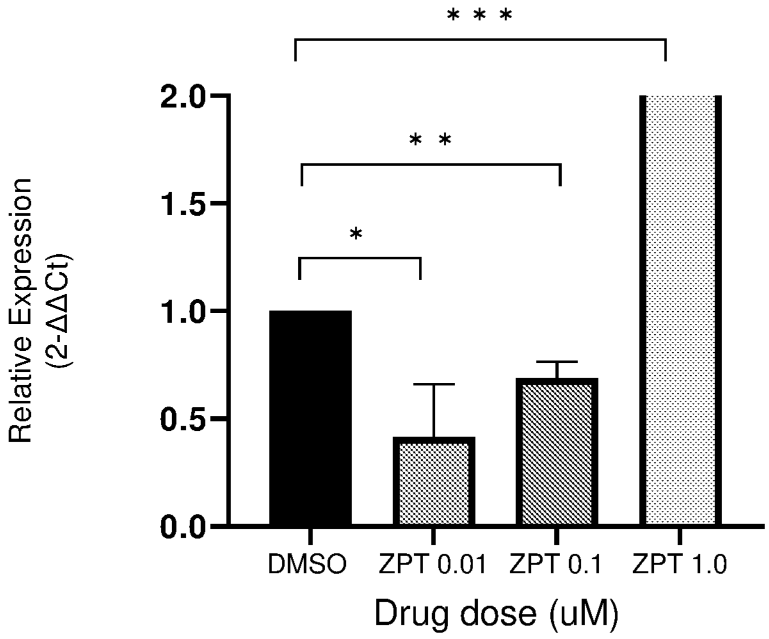

A $2^{nd}$ confirmatory screen was done using 1 μL drug concentration and vitamin D3 was confirmed to inhibit at low doses. (FIG. 6; FIG. 7)

Summary

Figure 3:
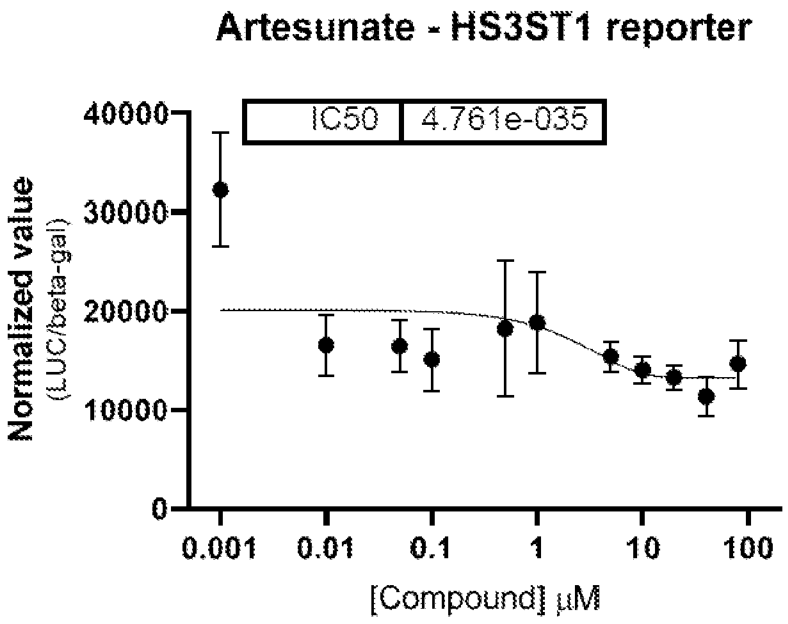
FIG. 3 shows an example artesunate-HS3ST1 reporter.
Figure 4:
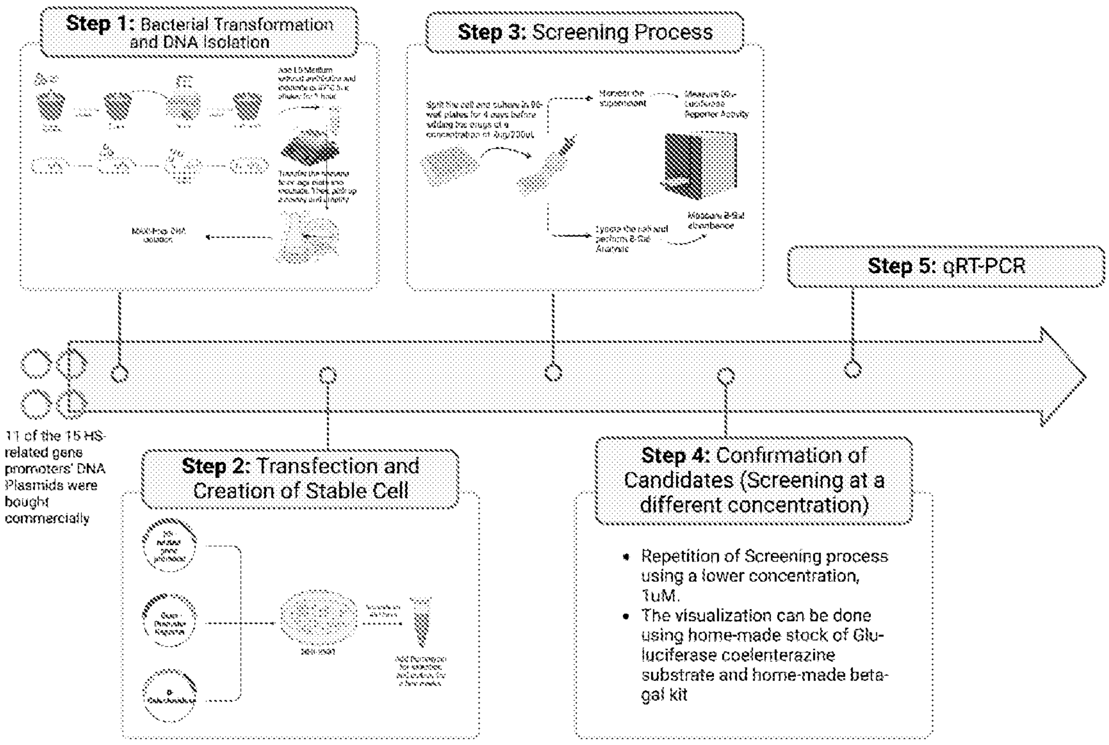
FIG. 4 shows the steps of the screening assay process.
Figure 5:
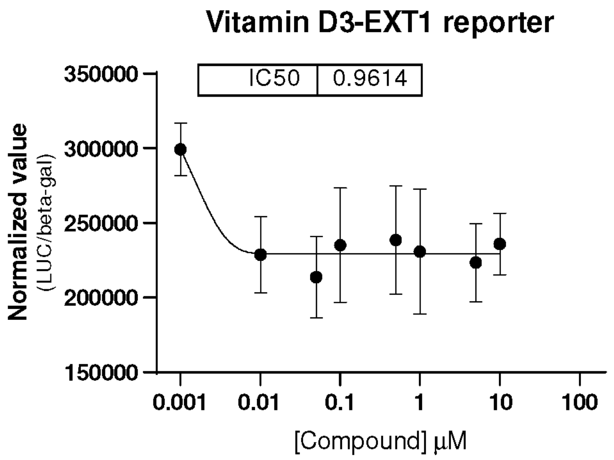
FIG. 5 shows an example vitamin D3-EXT1 reporter.

The HTS assay provided a new and effective approach to identify drugs that regulate the expression of HS-related genes. The EXT1 stable cell line showed high specificity in identification of EXT1 regulators. (FIG. 3) The EXT1 stable cell line shows high specificity in identification of EXT1 regulators. Pinpointed herein are specific drugs capable of selectively inhibiting HS gene expression without adversely affecting cell survival.

Figure 8:
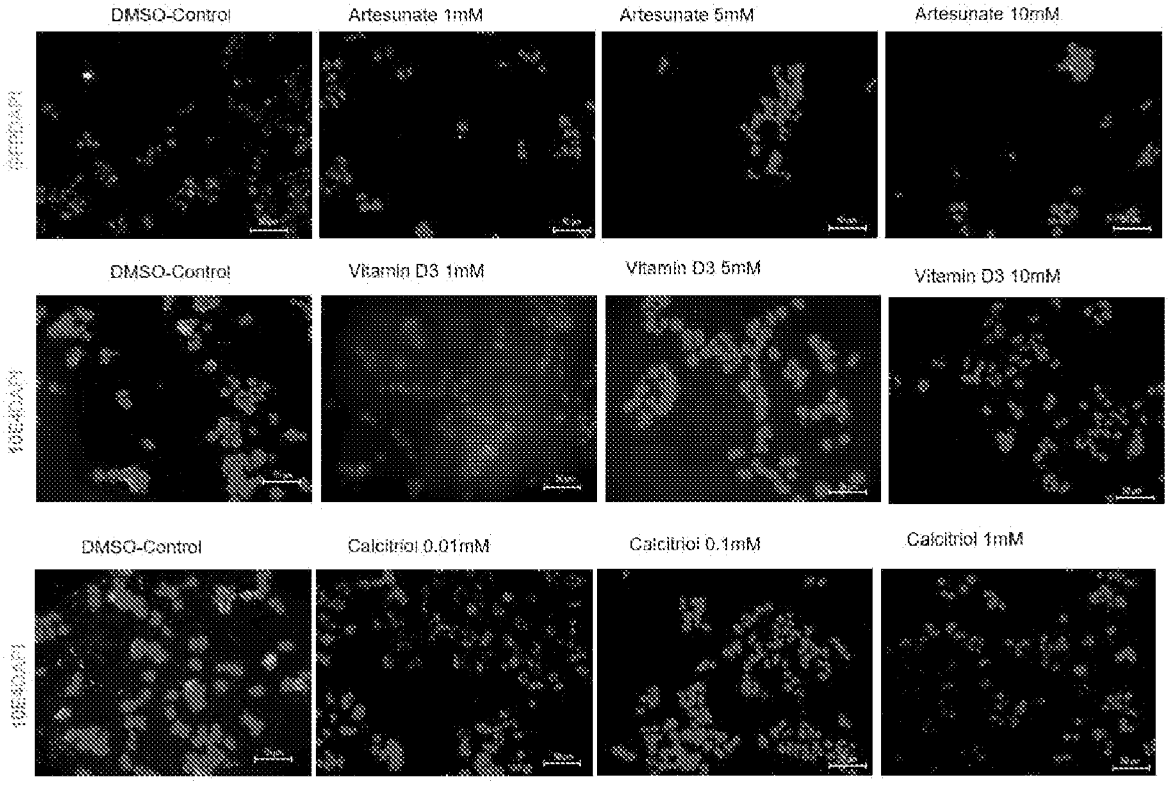
FIG. 8 shows immunostaining results of confirmed activation potential of FDA-approved drugs on heparan sulfate-related genes.
Figure 9A:
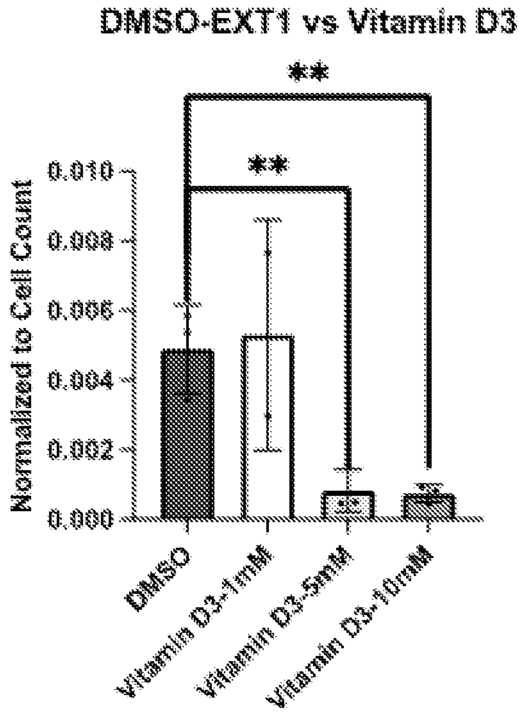
FIGS. 9A-9B show DMSO-EXT1 versus vitamin D3 (FIG. 9A) and calcitriol (FIG. 9B).
Figure 9B:
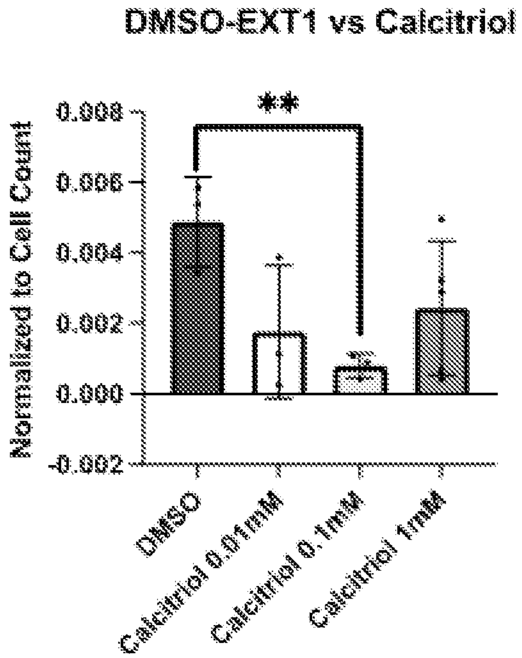
Figure 10A:
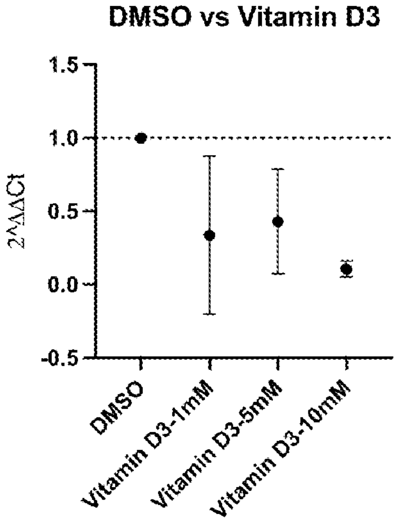
FIGS. 10A-10B show qRT-PCR results of confirmed activation potential of FDA-approved drugs on heparan sulfate-related genes for vitamin D3 (FIG. 10A), calcitriol (FIG. 10B), and artesunate (FIG. 10C). These experiments were performed using M17 cell line and incubated for 48 hours.
Figure 10B:
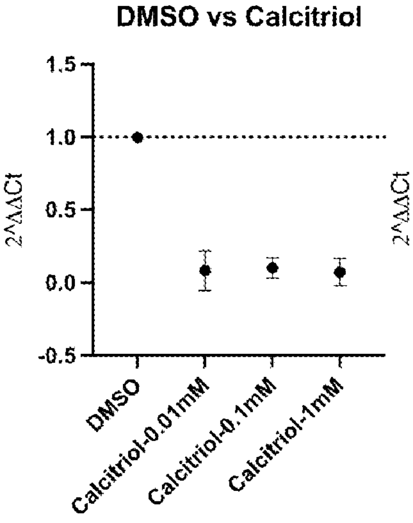
Figure 10C:
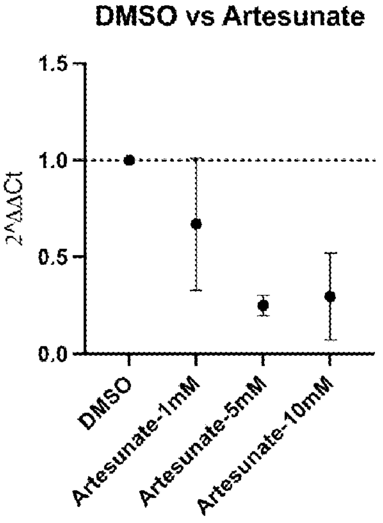
Figures 11A, 11B, 11C, 11D, 11E, 11F:
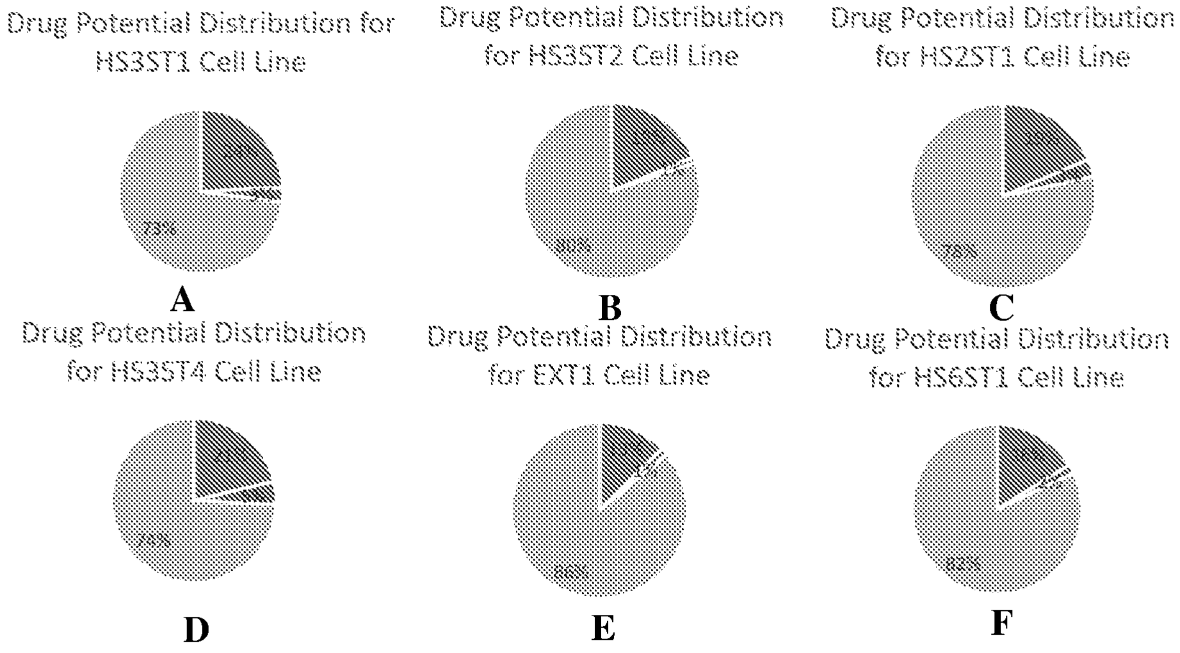
FIGS. 11A-11F show inhibition and activation potential of FDA-approved drugs on HS-related genes cell line.
Figures 12A, 12B, 12C, 12D, 12E, 12F:
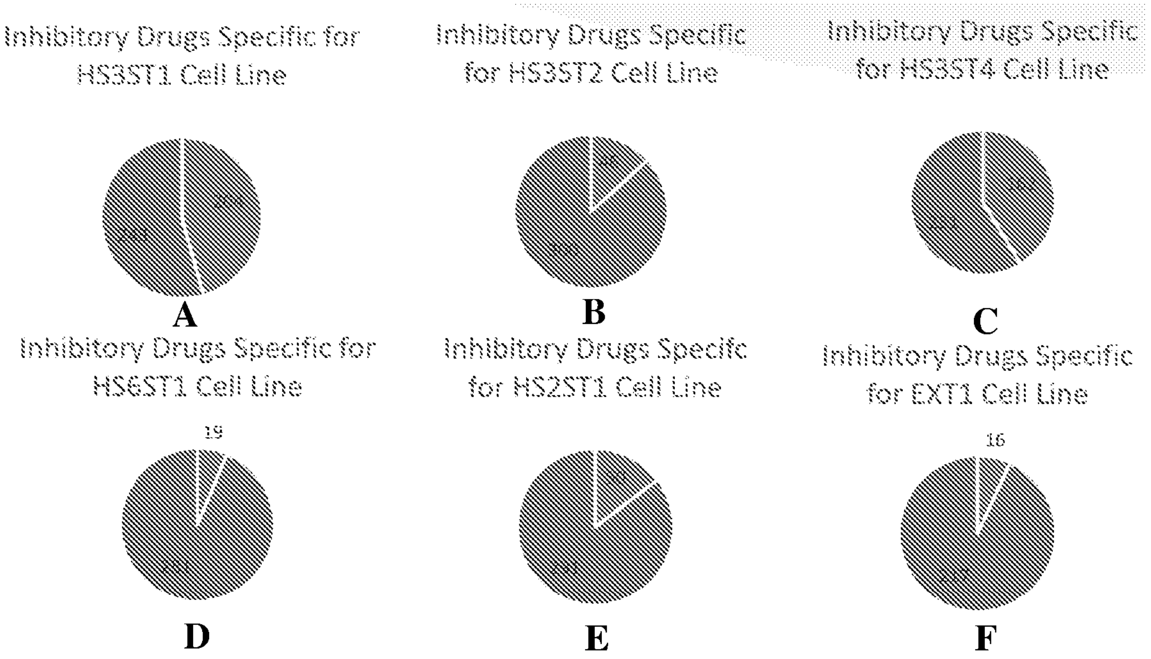
FIGS. 12A-12F show the inhibition potential of FDA-approved drugs on HS-related genes.
Figure 13A:
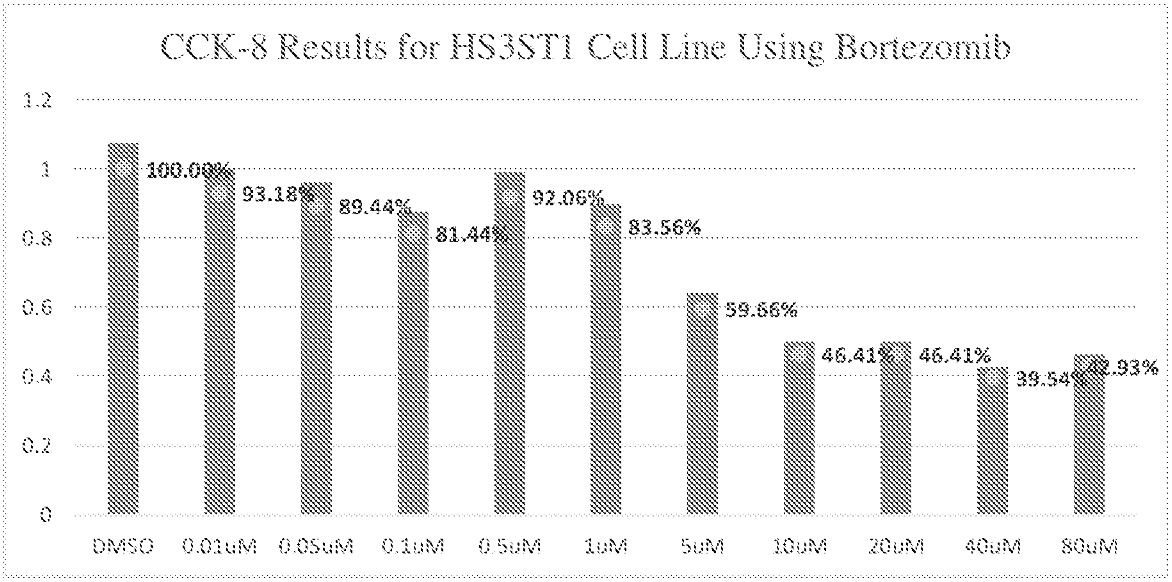
FIGS. 13A-13C show EC-50 and CCK-8 experiments on HS3ST1 using bortezomib.
Figure 13B:
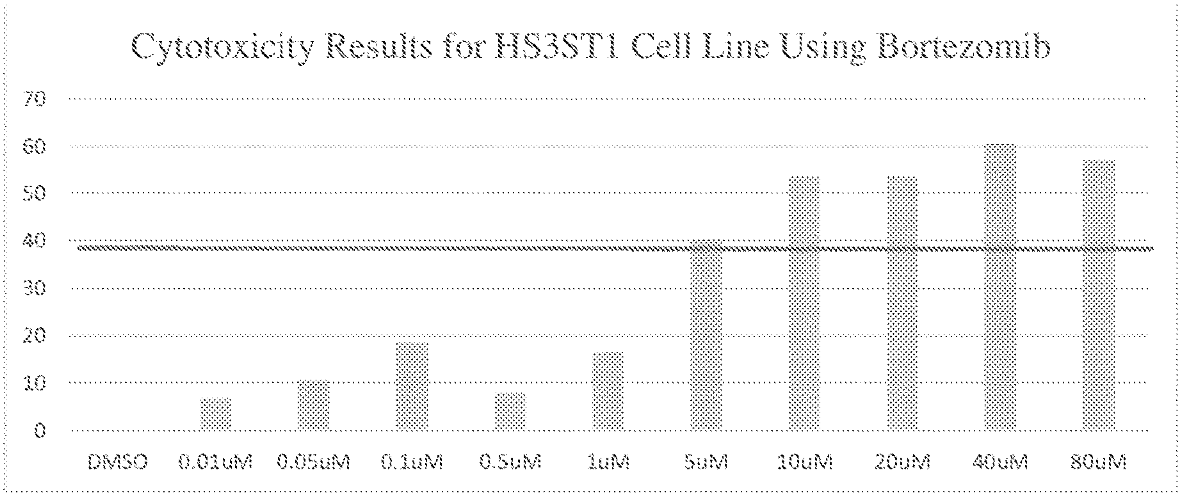
Figure 13C:
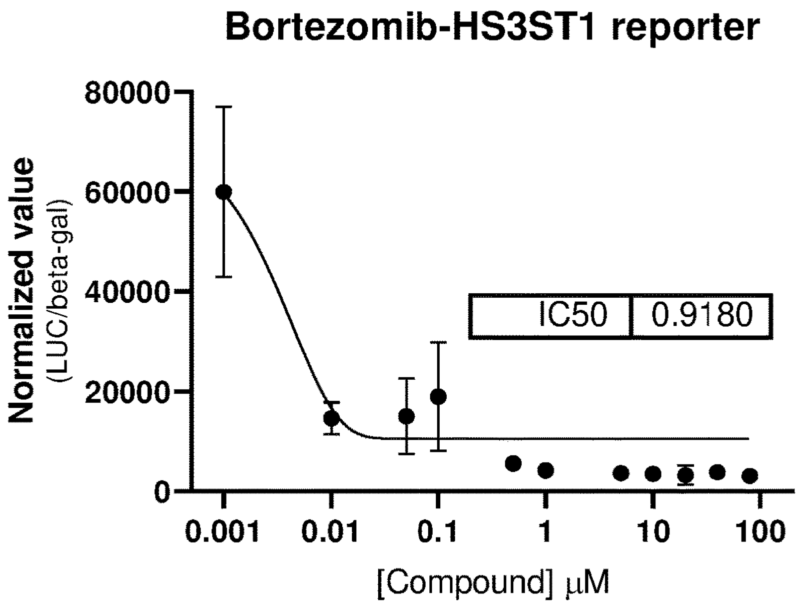
Figure 14A:
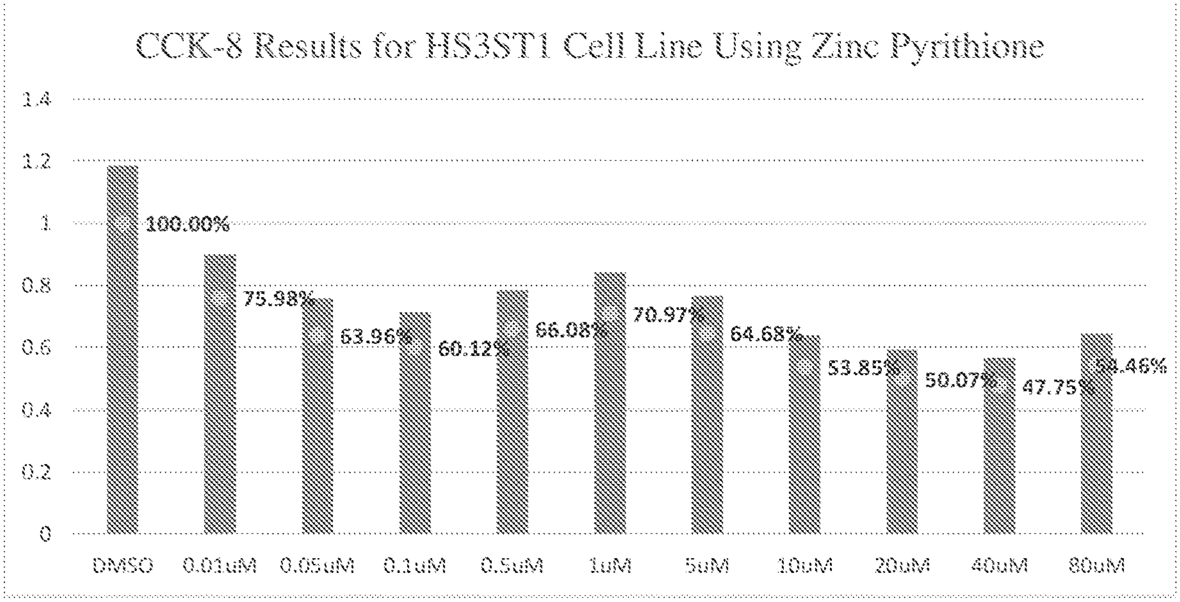
FIGS. 14A-14C show EC-50 and CCK-8 experiments on HS3ST1 using zinc pyrithione.
Figure 14B:
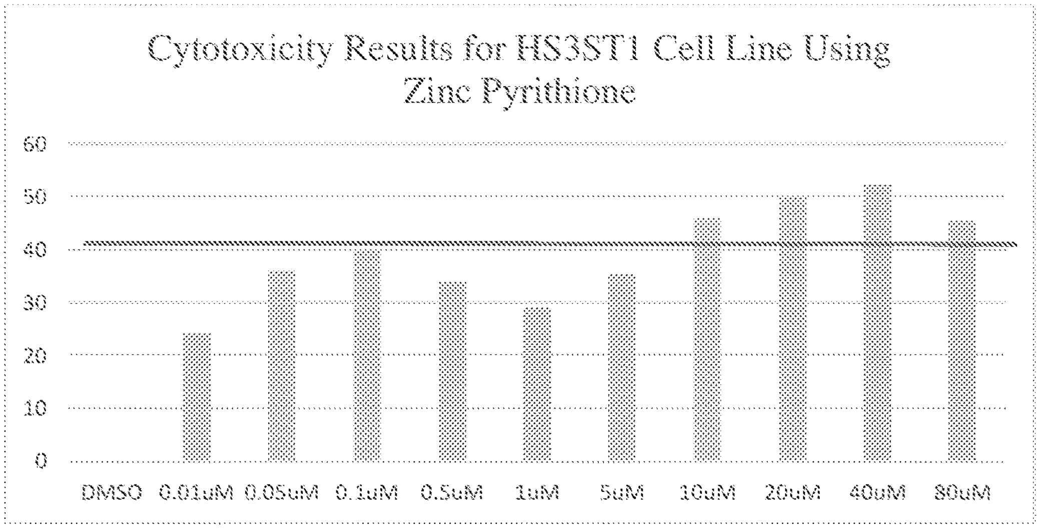
Figure 14C:
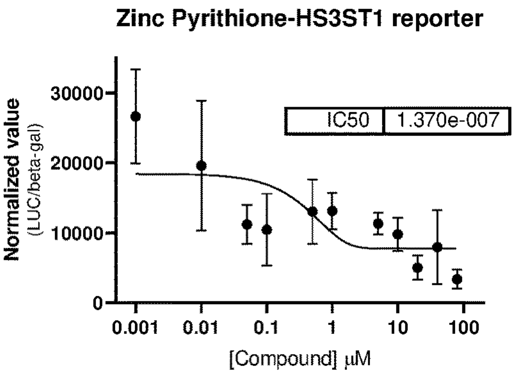
Figure 15A:
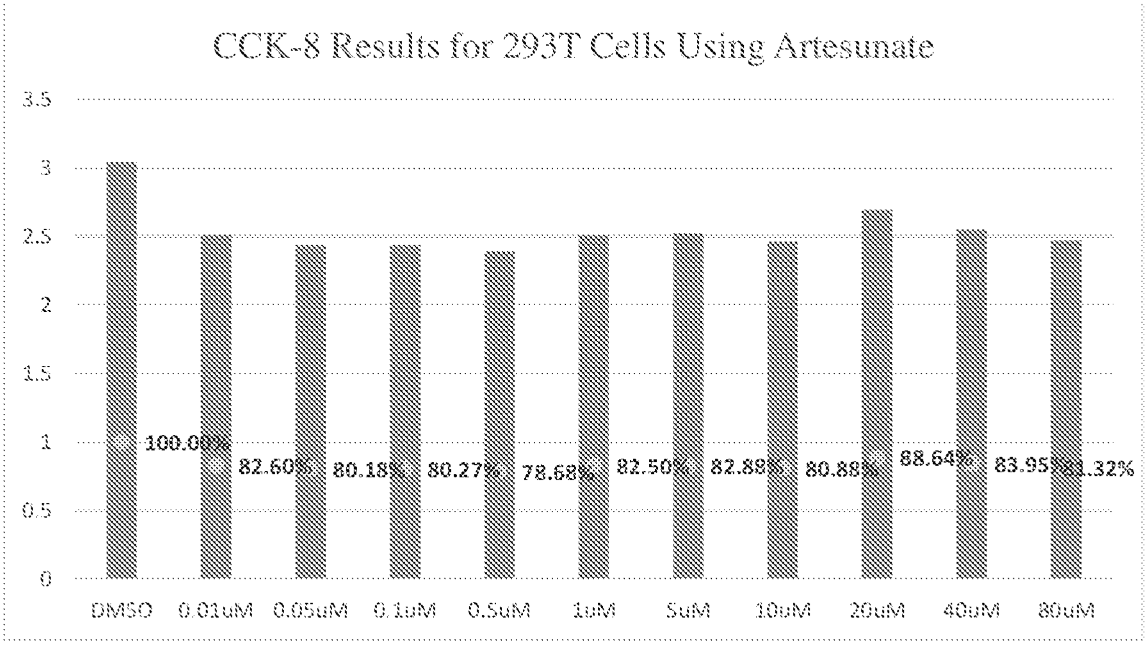
FIGS. 15A-15B show EC-50 and CCK-8 experiments on HS3ST1 using artesunate.
Figure 15B:
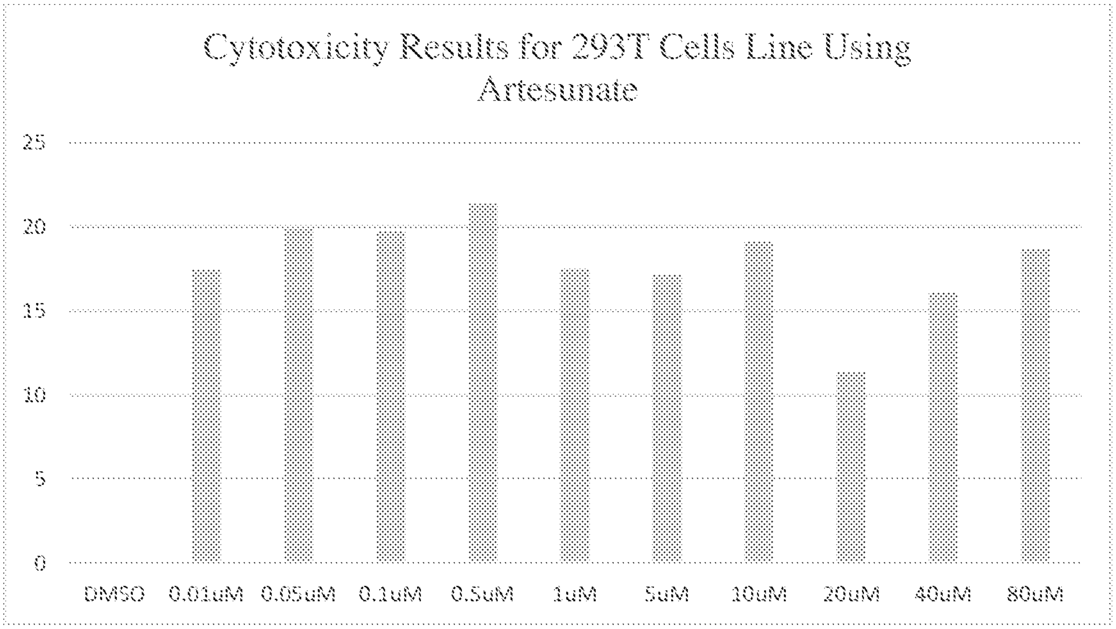

The experiments performed herein showed a dose-dependent inhibitory action of selected candidates on specific HS related genes. (FIG. 8; FIGS. 9A-9B; FIGS. 10A-10B)

Results

TABLE 1

Inhibition and activation FDA-approved Drug Candidates for Heparan Sulfate-Related Genes

| Cell Line | Library | Inhibition Candidate | Activation Candidate |
|---|---|---|---|
| HS3ST1 | L1021-01 | | BF, C10, G7, H8 |
| | L1021-02 | A8, A9, B3, B7, C4, H1, H4, H6 | H11 |
| HS3ST2 | L1021-01 | B4 | |
| | L1021-02 | C11 | |
| | L1021-03 | C11, G10 | |
| | L1021-04 | H3 | |
| | L1021-05 | A6 | G3 |
| | L1021-06 | F3, E6, E8, E9, F6, H6 | |
| | L1021-07 | A1, F4, H2, H3, H4, H8 | |
| | L1021-08 | B1, D4, D11 | |
| | L1021-09 | A11, B1, H7, H8 | C5 |
| | L1021-10 | G5, G8, H2 | |
| | L1021-11 | | |
| | L1021-12 | B6, H2 | B7 |
| | L1021-13 | A6, C5, C9, H5 | B1 |
| | L1021-14 | D9 | |
| | L1021-15 | | F6 |
| | L1021-16 | A1, C1, C2, C3, C6, C7, C8, C9, F1, F3 | |
| | L1021-17 | B6, H8 | |
| | L1021-18 | B9, D1, E5, F2, G7 | |
| HS3ST4 | L1021-01 | B4, C7, D3E3, E5-6, F1, F4-5, H1, H5 | C1 |
| | L1021-02 | C5, C7, D2, D6, G4-5, G8-9 | A7 |
| HS2ST1 | L1021-01 | F8, G10 | A1, A11, B10, B11, C3 |
| | L1021-02 | A8, A10, E8, F8, F11 | C1, C9 |
| | L1021-03 | A3, A10, B1, B3, B5, B12, F4, H4 | C7 |
| | L1021-04 | B4, F10 | C3, C4, C7 |
| | L1021-05 | C8, C9 | B5, E2, E4, E8, G9 |
| | L1021-06 | C8, C9 | |
| | L1021-07 | A7, D11, E2 | |
| | L1021-08 | A5, E4, E5 | C11, G2 |
| | L1021-09 | F1, F9, G5, G10 | A6, B5, G2 |
| | L1021-10 | F9 | |
| | L1021-11 | C2 | |
| | L1021-12 | | C1, G10 |
| | L1021-13 | G6, G11 | A1-4, B6, D8, E1-2, E7, F1-2, F4, F7-9, F11, G4, G10, H7 |
| | L1021-14 | A2, A4, E1, E4, E7, E10, F3, F8 | |
| | L1021-15 | E5, E6, E11 | |
| | L1021-16 | A3, D7, E8 | |
| | L1021-17 | B5, B7 | |
| | L1021-18 | | |
| HS6ST1 | L1021-01 | D6 | F11 |
| | L1021-02 | A9, F10 | |
| | L1021-03 | | C8 |

TABLE 1-continued

Inhibition and activation FDA-approved Drug Candidates for Heparan Sulfate-Related Genes

| Cell Line | Library | Inhibition Candidate | Activation Candidate |
|---|---|---|---|
| | L1021-04 | A4, A6, E2 | D11 |
| | L1021-05 | B1, B2, B7, B9, G6, G11 | A10 |
| | L1021-06 | | |
| | L1021-07 | C5 | |
| | L1021-08 | C2 | B2, B4, B5, B6, B8 |
| | L1021-09 | | A7, D11 |
| | L1021-10 | F4 | |
| | L1021-11 | E5, E9, F1, H7 | D7 |
| | L1021-12 | | |
| | L1021-13 | G3 | C4 |
| | L1021-14 | | A10, B9, D9, F6 |
| | L1021-15 | | D10 |
| | L1021-16 | D2 | A2-3, A5, A7, A11, B11, E7 |
| | L1021-17 | G11 | B1, D7, G2 |
| | L1021-18 | E2, H8 | A5, B1 |
| EXT1 | L1021-01 | | B1, B2, B3, B5 |
| | L1021-02 | C8, D6 | |
| | L1021-03 | E4 | |
| | L1021-04 | | |
| | L1021-05 | | |
| | L1021-06 | | |
| | L1021-07 | | |
| | L1021-08 | | H11 |
| | L1021-09 | A6, C2 | C11 |
| | L1021-10 | | |
| | L1021-11 | | |
| | L1021-12 | E6, F11 | |
| | L1021-13 | G8 | A5, A7 |
| | L1021-14 | A8, G6 | |
| | L1021-15 | A2, D1, D5 | |
| | L1021-16 | | |
| | L1021-17 | | |
| | L1021-18 | B5, B7 | A9, C5, E1, F2, H9 |

TABLE 2

Confirmation results of inhibition FDA-approved dug candidates for heparan sulfate-related genes at lower concentration.

| Cell Line | Library | Inhibition Candidate |
|---|---|---|
| HS3ST2 | | No Candidate |
| HS3ST1 | L1021-02 | B3-Bortezomib |
| | L1021-16 | D6-Zinc Pyrithione |
| | L1021-18 | A1-Artesunate |
| HS3ST2 | | No Candidate |
| HS3ST4 | L1021-11 | D5-Frosbretabullin |
| | L1021-17 | A6-Niclosamide |
| HS6ST1 | | No Candidate |
| EXT1 | L1021-15 | D5-Vitamin D3 |
| | L1021-16 | B2-Calcitriol |

Other advantages which are obvious, and which are inherent to the invention, will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

What is claimed is:

1. A method of decreasing heparan sulfate expression in a subject in need thereof, the method comprising administering an inhibitor of EXT1 gene expression, wherein the inhibitor comprises a therapeutically effective amount of vitamin D, and subsequently decreasing heparan sulfate expression by inhibiting EXT1.

2. The method of claim 1, wherein vitamin D is vitamin D3, calcitriol, or any combination thereof.

3. The method of claim 2, wherein vitamin D is vitamin D3.

4. The method of claim 2, wherein vitamin D is calcitriol.

5. The method of claim 1, wherein the therapeutically effective amount is from 0.2 microliters (μL) to 10 μL.

6. The method of claim 5, wherein the therapeutically effective amount is from 0.8 μL to 1.2 μL.

7. The method of claim 2, wherein the vitamin D3 has an IC50 value of from 0.9000 μM to 1.000 μM.

8. The method of claim 7, wherein the IC50 value is from 0.9500 μM to 0.9750 μM.

9. The method of claim 2, wherein the calcitriol has an IC50 value of from 0.9000 μM to 1.000 μM.

10. The method of claim 9, wherein the IC50 value is from 0.9500 μM to 0.9750 μM.

11. A method of treating cancer by decreasing heparan sulfate expression in a subject in need thereof, the method comprising administering an inhibitor of EXT1 gene expression, wherein the inhibitor comprises a therapeutically effective amount of vitamin D, and subsequently decreasing heparan sulfate expression by inhibiting EXT1.

12. The method of claim 11, wherein vitamin D is vitamin D3, calcitriol, or any combination thereof.

13. The method of claim 12, wherein vitamin D is vitamin D3.

14. The method of claim 12, wherein vitamin D is calcitriol.

15. The method of claim 11, wherein the therapeutically effective amount is from 0.2 microliters (μL) to 10 μL.

16. The method of claim 15, wherein the therapeutically effective amount is from 0.8 μL to 1.2 μL.

17. The method of claim 11, wherein the inhibitor is administered in combination with a cancer therapy.

18. The method of claim 17, wherein the cancer therapy comprises surgery, chemotherapy, immunotherapy, ionizing radiation, or a combination thereof.

19. The method of claim 11, wherein the method further comprises administering an additional therapeutic agent.

20. The method of claim 19, wherein the additional therapeutic agent comprises abiraterone acetate, apalutamide, bicalutamide, cabazitaxel, darolutamide, degarelix, docetaxel, enzalutamide, flutamide, goserelin acetate, leuprolide acetate, lutetium Lu 177 vipivotide tetraxetan, mitoxantrone hydrochloride, nilutamide, olaparib, radium 223 dichloride, relugolix, rucaparib camsylate, sipuleucel-t, or any combination thereof.

* * * * *